United States Patent

Pause

[11] Patent Number: 6,116,777
[45] Date of Patent: Sep. 12, 2000

[54] PROCEDURE AND DEVICE FOR THE MEASUREMENT OF THERMOPHYSICAL CHARACTERISTICS OF TEXTILES AND OTHER PLATE-LIKE MATERIALS

[76] Inventor: Barbara Hildegard Pause, 7161 Christopher Ct., Longmont, Colo. 80503

[21] Appl. No.: 08/924,906

[22] Filed: Sep. 8, 1997

[30] Foreign Application Priority Data

Sep. 10, 1996 [DE] Germany .................. 196 36 673

[51] Int. Cl.⁷ .................................................. G01N 25/00
[52] U.S. Cl. .......................................................... 374/43
[58] Field of Search .................. 374/29, 30, 31, 374/33, 43, 44, 45, 46; 73/159

[56] References Cited

U.S. PATENT DOCUMENTS

| | | | |
|---|---|---|---|
| 2,986,922 | 6/1961 | Garofalo et al. | 374/46 |
| 3,238,775 | 3/1966 | Watts | 374/30 |
| 4,259,859 | 4/1981 | Iida et al. | 374/43 |
| 4,722,609 | 2/1988 | Epstein et al. | 374/30 |
| 5,005,985 | 4/1991 | Piórkowska-Galeska et al. | 374/44 |

FOREIGN PATENT DOCUMENTS 1545148  2/1990  U.S.S.R. .................. 374/44

*Primary Examiner*—G. Bradley Bennett

[57] ABSTRACT

This invention provides a method for measurement of thermal characteristics of plate-like material samples, in particular textile materials, and a device for carring out such measurements.

18 Claims, 1 Drawing Sheet

PROCEDURE AND DEVICE FOR THE MEASUREMENT OF THERMOPHYSICAL CHARACTERISTICS OF TEXTILES AND OTHER PLATE-LIKE MATERIALS

BACKGROUND OF THE INVENTION

The use of textiles as thermal insulators has become increasingly important during the last few years. Textiles differ from other solid material in that they have an air volume, enclosed in fiber spaces, in addition to the solid fiber material. In general, air is known to be a very good thermal insulator. The air content in a textile, which is usually high, provides a very good thermal insulation effect. However, the good thermal insulation effect of textiles is lost to a considerable degree, if for instance the air volume decreases as the textile is being compressed, if the textile absorbs water or vapor from the environment, or if it is heated. Since climatic conditions of the environment, i.e. temperature as well as humidity, may frequently change during the use of a textile as a thermal insulator, and since in addition the material is often compressed during processing, knowing the thermophysical characteristics of textiles under various anticipated application conditions is a prerequisite for its appropriate use and continued assurance of the required thermal insulation effect.

However, in the known test procedures for the determination of the thermophysical characteristics of textile materials, the stated requirements are hardly met. In most instances, the thermophysical characteristics are determined only for material temperatures within the range of the room temperature. In this test procedure, the material samples are heated on one side, and the temperature on the backside of the material is kept constant at a value corresponding to the room temperature. Most of the known measuring procedures are based on stationary measuring principles, in other words, the actual measurement is taken only when a constant thermal flow through the material sample is achieved, i.e. a constant temperature difference exists between the two sample surfaces. Setting this stationary state of equilibrium can take several hours. During this long-term heat application, the moisture content of material, which was wet or damp before measurements began, may change considerably. Therefore, these known procedures are suitable only for investigations of dry material samples.

One essential disadvantage of a number of known single-plate methods is that the material sample is placed onto the heating plate without any special attachment, so that frequently an air cushion may be formed between the heating plate and the material sample, resulting in false measuring results. In the known two-plate method, the material sample is arranged between two plates, one of which functions as a heat source and the other functions as a heat sink. The upper of the two plates exerts vertical contact pressure on the material sample which can result in an essential decrease in material thickness, for example in loosely structured samples. However, the resulting change in material thickness is not considered in the determination of thermophysical characteristics, which again leads to considerable measuring errors.

In addition, the contact pressure cannot be varied in all known measuring procedures for the determination of thermophysical characteristics of textile materials, so that it is impossible to conduct appropriate practical investigations. Another disadvantage of the known measuring procedures is that measurements cannot be carried out on very thin samples, since it is impossible to achieve a stationary temperature difference between the two sample surfaces. Therefore, materials with thicknesses in a range of millimeters are usually investigated in several layer packs with this procedure, resulting again in increased measuring errors, since air cushions may form between the material layers.

SUMMARY OF THE INVENTION

The subject of the invention is a procedure and device for the determination of the thermophysical characteristics of plate-like samples, in particular textile materials, under various test conditions. In the procedure, two samples of the test material are arranged symmetrically with respect to a surface heater. In the measuring process the material samples are first heated over a short period of time through the surface heater and subsequently cooled for an equally long time interval without any outside influences. Temperature measurements are taken on the sample surface adjacent to the surface heater. The thermophysical characteristics, i.e. thermal conductivity, thermal resistance, temperature conductivity and specific heat capacity of the test material are determined from the temperature measurements, the applied heat flux, as well as the thickness and density of the material. The determination of the thermophysical characteristics is always made under exactly determined testing conditions, characterized by the material temperature, the moisture content of the material, as well as the thickness and the density of the material under a predetermined contact pressure. For investigations where the environmental temperature differs from the material temperature, the material samples are attemperated prior to measuring. According to the invention, attemperation is carried out in the measuring chamber, containing the test pack, consisting the heat source, the material samples and the temperature sensors during the measuring process. The investigation of the material samples is always conducted under a constant contact pressure, generated according to the invention by means of a pressure spindle, which is measured by a load cell and can be varied. Under the contact pressure exerted on the material sample, the exact sample thickness is measured by means of a displacement transducer, and the material density is determined from the thickness and the known sample weight. Also, the current moisture content of the material can be continuously recorded by means of a surface electrode during the investigation.

DETAILED DESCRIPTION

Figure 1:
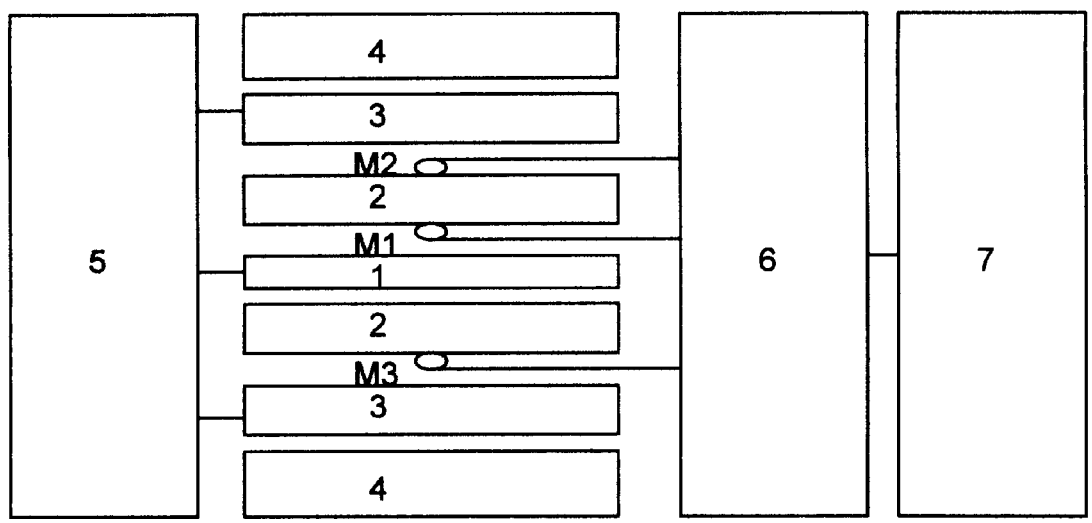
FIG. 1 is a diagram of the basic setup of the device
Figure 2:
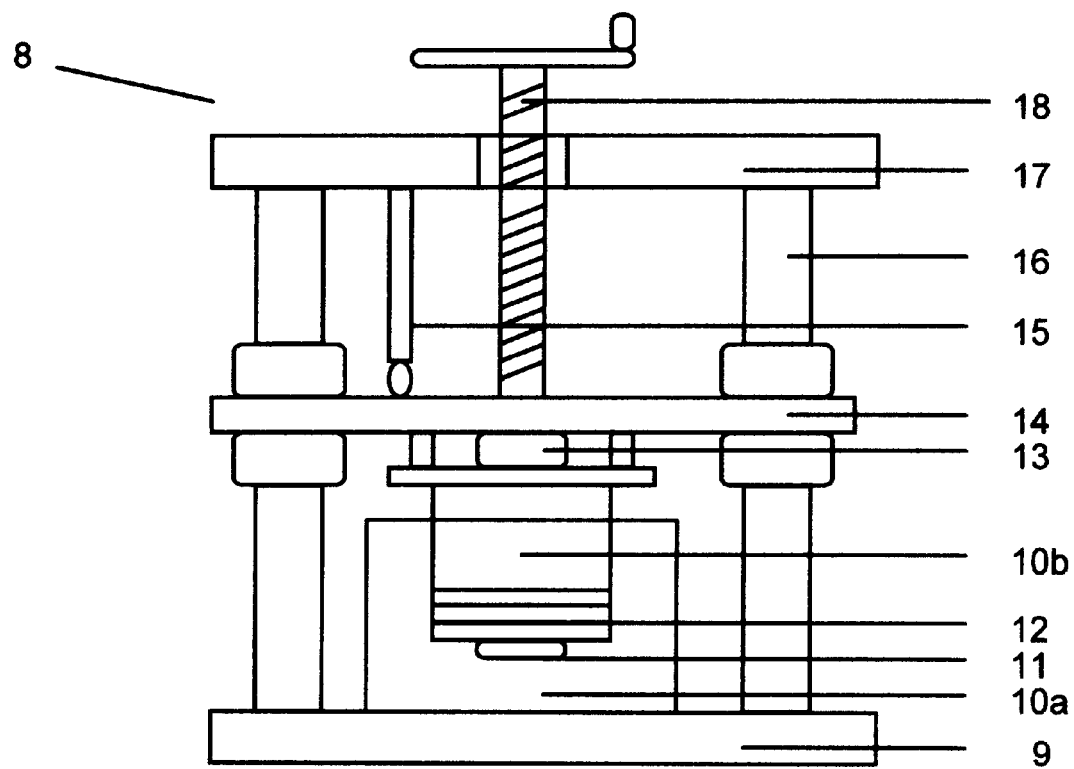
FIG. 2 is a sectional view of the measuring unit equipped with the measuring chamber in variation 1

The subject of the invention is a procedure and device for the determination of the thermophysical characteristics of plate-like samples, in particular textile materials, under various test conditions. In the process, the thermophysical characteristics, i.e. thermal conductivity, thermal resistance, temperature conductivity and specific heat capacity of the test material are detected for predetermined test conditions as well. Preferably, the invention is used in the investigation of textiles, however, it is appropriate for the determination of the thermophysical characteristics of all materials of which plate-like material samples can be produced. For example, the procedure and the device of the invention have been used successfully in test measurements of textiles, foam insulators, fiberboards, leather and films.

The purpose of the invention is to provide a procedure and a device for the determination of thermophysical characteristics, in particular for textile materials, under practical measuring conditions with a high measuring accuracy. In addition, compared to the known measuring procedures, the measuring times are expected to be considerably shorter with the procedure according to the invention, which in particular allows the investigation of wet material samples. With the device according to the invention, it will be possible to investigate material samples of very different thicknesses, in particular very thin material samples. In addition, compared to the known measuring procedures, the required amount of test material will be less, due to the considerable reduction of the sample surface.

The nature of the invention is based on a non-stationary measuring principle, where two material samples with equal dimensions, arranged symmetrically with respect to a surface heater, are alternately subjected to heating and cooling processes. On the sample surface adjacent to the surface heater the temperature run during the heating and the cooling process is measured. The thermophysical characteristics are determined from selected temperature measurements, the applied heat flux, as well as the thickness and density of the samples.

During the heating process, the surface heater (1) generates a constant heat flux over a short period of time in the direction of the sample surface normals. To avoid undesirable heating after the turn off of the heater its heat capacity and heat transfer resistance should be small. This is obtained by using a very thin surface heater which possesses a small inherent mass.

Prior to measuring, the two material samples (2) are in an isothermic original state. During measuring, the material samples (2) are first heated on one side by means of the surface heater (1) for a given time interval. When the heat source is turned off at the end of the given heating time, a cooling of the material sample occurs during the measuring process, without any external influence, for an equally long time interval. The duration of the heating process is obtained from the boundary conditions assumed for the measuring process, usually less than one minute. According to the concept of the procedure, the temperatures of the material surfaces facing away from the heat source are to remain constant throughout the entire measuring procedure (heating and cooling), i.e., the applied heat is intended to enter but not penetrate the test materials. Thus, according to the invention the continuous, stationary heat application, which is the basis for known procedures, is replaced by an short-time, non-stationary heat application. During measuring, the temperature curve in the heating surface is continuously recorded at measuring point M1. The two additional temperature measuring points M2 and M3, both located on the surfaces of the material samples facing away from the heat source, serve only to control the material temperature prior to measurement, as well as to retain the boundary conditions the procedure is based on during the measuring process.

The determination of thermal conductivity $\lambda$ of the test materials is based on the end temperatures $\theta_{01}$ and $\theta_{02}$, achieved during the heating and cooling process, resp., and the applied heat flux $\Phi$, as well as the material thickness D. The thermal conductivity is obtained through $$\lambda = \frac{\Phi D}{2} \frac{\vartheta_{01} - \vartheta_{02}}{\vartheta_{01}^2}.$$

The thermal resistance $R_c$ is determined according to the known equation $$R_c = \frac{D}{\lambda}.$$

The temperature conductivity a is determined through two temperature measuring values $\theta_{02}$ and $\theta_{03}$ obtained on the sample surface adjacent to the surface heater during the cooling process, the associated cooling times $t_2$ and $t_3$, as well as the material thickness D. $\theta_{02}$ is the end temperature of the cooling process, with $t_2$ as the associated measuring time. $\theta_{03}$ is the temperature measurement, obtained after the cooling process is half-way completed, with $t_3$ as the associated measuring time. The temperature conductivity a is calculated through $$a = \frac{2D^2}{\pi^2} \frac{\ln[\vartheta_{03}/\vartheta_{02}]}{t_2 - t_3}.$$

The specific heat capacity c is obtained through the thermal conductivity $\lambda$, the temperature conductivity a and the material density $\rho$, using the known equation $$c = \frac{\lambda}{a\rho}.$$

The material density $\rho$ is calculated from thickness and weight of the sample.

The determination of the thermophysical characteristics of the material samples according to the invention is always made under exactly defined test conditions with respect to the temperature and moisture content of the material, the contact pressure, as well as the material thickness and material density resulting from the contact pressure. With the known measuring procedures, this contributes considerably to an improved measuring accuracy and allows exact material comparisons. For the determination and control of the test condition, the material temperature, the moisture content of the material and the contact pressure affecting the material samples, as well as the material thickness present under this contact pressure, are determined prior to measuring, and the material density is calculated from the material thickness and the sample weight. Due to the heating in a short period of time in this measuring process, the moisture content of the material remains constant during the measurement, even in wet material samples. Thus, an exact determination of the thermophysical characteristics of wet material sample is possible. Furthermore, the measuring process allows the investigation of material samples with a thickness of less than one millimeter and a considerable reduction in the size of the material sample. Due to the minimum contact pressure, which is realized when no given values exist in this respect, a direct contact between the material samples and the surface heater is ensured, thus preventing the formation of air cushions between the material sample and the heat source, resulting in greater measuring accuracy.

The device according to the invention for the realization of the measuring procedure consists of a measuring unit (8), a power supply unit (5), a measuring amplifier and control unit (6), as well as a computer system (7) for the recording of measuring values and their evaluation (FIG. 1).

The core of the measuring unit (8) is a measuring chamber, containing the test pack (12), consisting of the two material samples (2), during the measuring process, the surface heater (1), located between them, and the temperature sensors. In order to prevent undesirable heat losses to the environment during the measuring process, the measuring chamber is within a casing (4) of heat insulating material.

In order to meet various measuring requirements while maintaining a basic setup, three different exchangeable measuring chamber types were provided according to the invention. The basic type (measuring chamber variation 1) is used for investigations where the material temperatures are equal to the environmental temperature. This chamber variation is equipped with a moisture sensor (11), with which the ma moisture content of the test sample can be recorded, prior to the measuring as well as continuously throughout the measuring process. This measuring chamber is used in particular for the investigation of wet or damp material samples.

In the determination of the thermophysical characteristics of material samples with temperatures deviating from the environmental temperature, within a temperature range of −30° C. to approximately 200° C., measuring chamber variation 2 is equipped with a heating/cooling system (3), with which material samples can be heated or cooled to the desired initial temperature prior to the investigation.

Measuring chamber variation 3 is used for investigations where the material temperatures are higher than 200° C. and includes high temperature heating elements (3) to heat material samples to the desired initial temperature. This type of measuring chamber has a casing, which should preferably be equipped with reinforced heat insulation, as well as a cooling system for heat removal, in order to prevent strong heat dissipation from the surface of the measuring chamber and thus protect for instance the load cell against damaging overheating.

All measuring chamber variations consist of two parts (10a and 10b), arranged vertically on top of each other within the measuring unit. The lower part of the measuring chamber (10a) is mounted immovably on the base plate (9) of the column guide frame (16). The upper part of the measuring chamber (10b) is attached to a vertically shiftable metal plate (14), where the vertical movement is carried out by means of a pressure device, e.g. a pressure spindle (18). Due to the two-part design of the measuring chamber and the ability to slide both parts vertically against each other, material samples of varying thickness can be included in the investigation, since the height of the chamber inside space can thus be varied as desired. In addition, the material samples can be easily exchanged in this way.

If the measuring chamber (10a and 10b) is closed, the desired contact pressure is applied to the material samples by means of the pressure spindle (18) in the direction of the surface normals. This contact pressure is preferably kept constant by means of a locking device throughout the measuring process. Due to the effect of the contact pressure, the formation of air gaps between the surface heat source and the material samples is prevented from the start, resulting in a considerable improvement of the measuring accuracy, as compared to the known procedures. The contact pressure is detected by the load cell (13), mounted between the middle metal plate (14) and the upper chamber part (10b). A displacement transducer (15) is used to determine the material thickness under the given contact pressure. The displacement transducer (15) records the vertical shift of the middle metal plate (14) in relationship to the upper fixed metal plate (17).

The distance determined between the metal plates (14) and (17) serves as the basis for the calculation of the exact material thickness under the given measuring conditions, which has a direct influence on the determination of the thermophysical parameters. In addition, the determined material thickness is the basis for the determination of the material density. By determining both measuring values under the test conditions given for the measuring process, the measuring accuracy is considerably improved, as compared to the known measuring procedures.

In the measurement of temperatures, resistance thermometers are used, whose design is surficial as well, and which are attached directly onto the sample surfaces, the heating/cooling elements or the chamber walls.

Measuring with the proposed device is conducted as follows:

The measuring unit (8) is equipped with the measuring chamber (10a and 10b), required for the realization of the measuring task. At the same time, the measuring programm for the detection and evaluation of the measuring data and control of the measuring process is loaded. After attachment of the temperature sensors, the prepared material samples (2), conditioned under a given humidity, are placed into the measuring chamber (10a and 10b), together with the surface heater (1). The measuring chamber is closed, and the contact pressure, intended for the measuring, is generated by means of the pressure spindle (18). Using the displacement transducer (15), the distance between the upper (17) and middle metal plates (14) of the column guide frame (16) is measured, and the thickness and density of the material samples under the given contact pressure are calculated through an autosequential data set of the measuring program. The determination of the moisture condition of the material samples is made either prior to measuring outside of the measuring chamber with a suitable measuring method, or during the measuring process within the measuring chamber by means of a moisture sensor (11). The latter option is used in particular when damp or wet samples are to be investigated under a defined moisture condition. In these investigations, the material temperature is equal to the environmental temperature, i.e. the material samples are not first attemperated.

If, however, thermophysical characteristics are to be determined when the material temperature of the test materials differs from the environmental temperature, the measuring system is attemperated prior to the measuring process, i.e. it is heated or cooled by means of the heating/cooling system (3) of the respective measuring chamber variation. When an isothermic state is reached within the material samples after the external heating/cooling elements are turned off, the actual measuring is begun by heating the material samples by means of the surface heater (1) of the test pack (12). When a given end temperature is reached, the heater is turned off through a control program. The measuring process is continued by cooling the material samples and terminated after a time interval equal to that of the heating process has expired.

The thermophysical characteristics of the test samples under the given test conditions are determined by means of a computer program, based on the temperature curve obtained in the heating surface, the applied heat flux, as well as the material thickness and density.

The setup of the device according to the invention is simple and easy to operate. Compared to the known measuring procedures, the measuring procedure according to the invention is distinguished by a high degree of accuracy and considerably shorter measuring times, and it is suitable in particular for investigations of very thin material samples as well as damp and wet samples.

What is claimed:

1. A process for simultanous determination of two or more thermophysical characteristics of plate-like samples, in particular textile materials, which has the steps of:
   (a) arranging two material samples of equal thicknesses and known weights symmetrically with respect to a surface heater;
   (b) heating the samples for a selected period of time and subsequently cooling the samples without an outside influence for the same period of time while measuring the temperature at the material surface adjacent to the surface heater of at least one of the material samples;
   (c) calculating two or more thermophysical characteristics of the material samples using the temperature measurements as a function of time, the sample thickness and the sample weight, as well as the heat flux applied to the samples by the surface a heater.

2. The process according to claim 1 where the thermophysical characteristics are thermal conductivity, thermal resistance, temperature conductivity and specific heat capacity.

3. The process according to claim 1 where the thermal conductivity is calculated using end temperatures measured during the heating and the cooling process on the sample surface adjacent to the surface heater as well as heat flux applied to the samples and the sample thickness.

4. The process according to claim 1 where the temperature conductivity is determined using two temperature measurements obtained on the sample surface adjacent to the surface heater during the cooling process of the samples, the associated cooling times of the temperature measurements and the material thickness.

5. The process according to claim 1 where heating of the material samples is carried out only from one side with a constant heat flux density.

6. The process according to claim 5 where the heat applied to the samples only enters the samples but does not penetrate them so that the temperature on the sample surface away from the heater remains constant.

7. The process according to claim 1 where the temperature measurement for the determination of the thermophysical characteristics of the samples is made at the surface of the material sample adjacent to the surface heater (at point M1, in FIG.1) and the temperature measurements at the sample surfaces facing away from the surface heater (at points M2 and M3, in FIG. 1) are used to deter mine the sample temperature prior to the measuring process and to control the temperature run during the measuring process to assure that the temperature at the sample surfaces facing away from the surface heater remains constant.

8. The process according to claim 1 which allows to determine the thermophysical characteristics of the test samples at selected and exactly defined material conditions including the material temperature at the beginning of the measurement, the material moisture content, the contact pressure, as well as the material thickness and density resulting from the contact pressure.

9. The process according to claim 1 where the moisture content of the sample as well as the contact pressure applied to the sample is kept constant during the measurement.

10. The process according to claim 1 where the moisture content of the sample, the contact pressure applied to the sample and the sample thickness are determined prior and during the measuring process.

11. A device for measuring thermophysical characteristics of material samples where two material samples are arranged symmetrically with respect to a surface heater which serves to heat the material samples during a measuring process, having a measuring unit with a measuring chamber to receive a test pack, consisting of the surface heater, the two material samples and the temperature sensors where the measuring chamber is equipped with surficial heating and cooling elements for an attemperation of the material samples and with a moisture sensor.

12. The device according to claim 11 where the measuring chamber consists of two parts, arranged vertically on top of each other; and where in addition the upper part can be shifted vertically.

13. The device according to claim 12 where the measuring chamber is enclosed in a casing of heat insulating material and is also provided with a cooling system for thermal dissipation in case of overheating.

14. The device according to claim 11 where the measuring unit is equipped with a pressure generating device with which a contact pressure can be applied to the material samples in the direction of the surface normals.

15. The device according to claim 14 where the measuring unit contains a load cell for the determination of the contact pressure on the material samples.

16. The device according to claim 11 where the measuring unit contains a displacement transducer for the determination of the sample thickness.

17. The device according to claim 11 where the temperature sensors are resistance thermometers.

18. The device according to claim 11 further having an amplification and a control system as well as a computer for recording and processing of the measured values.

* * * * *